US009470634B1

(12) United States Patent
Anderson

(10) Patent No.: US 9,470,634 B1
(45) Date of Patent: Oct. 18, 2016

(54) ELECTRIDE MEDIATED SURFACE ENHANCED RAMAN SCATTERING (SERS)

(71) Applicant: United States of America as Represented by the Administrator of NASA, Washington, DC (US)

(72) Inventor: Mark S. Anderson, La Crescenta, CA (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 171 days.

(21) Appl. No.: 14/101,547

(22) Filed: Dec. 10, 2013

(51) Int. Cl.
*G01J 3/44* (2006.01)
*G01N 21/65* (2006.01)
*G01N 21/01* (2006.01)
*H01L 51/50* (2006.01)

(52) U.S. Cl.
CPC .............. *G01N 21/658* (2013.01); *G01J 3/44* (2013.01); *G01N 21/01* (2013.01); *H01L 51/5012* (2013.01)

(58) Field of Classification Search
CPC ....... G01N 21/658; G01N 21/01; G01J 3/44; H01L 51/5012
USPC .......... 356/301; 435/6, 29, 39, 287.1, 287.2, 435/287.7, 283.1, 306.1; 252/519.1, 519.4, 252/62.2; 313/309, 486, 496
See application file for complete search history.

(56) References Cited

U.S. PATENT DOCUMENTS

| | | | | |
|---|---|---|---|---|
| 3,811,062 A | * | 5/1974 | Andoh | H01J 11/00 313/586 |
| 5,675,972 A | * | 10/1997 | Edelson | F25B 21/00 313/310 |
| 6,103,298 A | * | 8/2000 | Edelson | C23C 14/12 427/126.2 |
| 6,644,036 B2 | * | 11/2003 | Suthoff | F25B 21/00 62/3.1 |
| 7,498,507 B2 | * | 3/2009 | Weaver, Jr. | H01L 35/32 136/200 |
| 7,601,507 B2 | * | 10/2009 | O'Connor | B82Y 15/00 435/7.1 |
| 8,858,883 B2 | * | 10/2014 | Dowling et al. | 422/68.1 |
| 2002/0151041 A1 | * | 10/2002 | Kreimer et al. | 435/287.2 |
| 2004/0217331 A1 | * | 11/2004 | Lussey | G01N 27/126 252/500 |
| 2007/0178477 A1 | * | 8/2007 | Joiner et al. | 435/6 |
| 2008/0030137 A1 | * | 2/2008 | Yoshioka | H01J 11/12 313/584 |
| 2009/0242405 A1 | * | 10/2009 | Mayer et al. | 204/435 |
| 2010/0038023 A1 | * | 2/2010 | Kho | B32B 17/06 156/247 |
| 2010/0049021 A1 | * | 2/2010 | Jina et al. | 600/345 |
| 2011/0155227 A1 | * | 6/2011 | Yagi et al. | 136/252 |

(Continued)

OTHER PUBLICATIONS

"Surface-Enhanced Raman Scattering," A. Campion and P. Kambhampati, Chem. Soc. Rev. 27(4), 241-250 (1998).

(Continued)

*Primary Examiner* — Sang Nguyen
(74) *Attorney, Agent, or Firm* — Mark Homer

(57) ABSTRACT

An electride may provide surface enhanced Raman scattering (SERS). The electride, a compound where the electrons serve as anions, may be a ceramic electride, such as a conductive ceramic derived from mayenite, or an organic electride, for example. The textured electrode surface or electride particles may strongly enhance the Raman scattering of organic or other Raman active analytes. This may also provide a sensitive method for monitoring the chemistry and electronic environment at the electride surface. The results are evidence of a new class of polariton (i.e., a surface electride-polariton resonance mechanism) that is analogous to the surface plasmon-polariton resonance that mediates conventional SERS.

19 Claims, 10 Drawing Sheets

(56) References Cited

U.S. PATENT DOCUMENTS

| | | | |
|---|---|---|---|
| 2011/0155970 A1* | 6/2011 | Ito et al. | 252/519.14 |
| 2012/0064567 A1* | 3/2012 | Stakenborg et al. | 435/39 |
| 2013/0183224 A1* | 7/2013 | Hosono et al. | 423/363 |

OTHER PUBLICATIONS

"Locally Enhanced Raman Spectroscopy with an Atomic Force Microscope," M. S. Anderson. Appl. Phys. Lett. 76(21), 3130-3132 (2000).

"Enhancement of the Infrared Absorption from Molecular Monolayers with Thin Metal Overlayers," A. Hartstein, J. R. Kartley, and J. C. Tsang, Phys. Rev. Lett. 45(3), 201-204 (1980).

"Surface-Enhanced Vibrational Spectroscopy," R. Aroca, Surface Enhanced Vibrational Spectroscopy (Wiley, Hoboken, NJ, 2006).

"Raman Spectra of Pyridine Adsorbed at a Silver Electrode," M. Fleischmann, P. J. Kendra, and A. J. McQuillan, Chem. Phys. Lett. 26(2), 163-166 (1974).

"Surface-Roughness and Enhanced Intensity of Raman-Scattering by Molecules Adsorbed on Metals," M. Moskovits, J. Chem. Phys. 69(9), 4159-4161 (1978).

"Enhanced Infrared Aborption with Dielectric Nanoparticles," M. S. Anderson, Appl Phys. Lett. 83(14), 2964-2965 (2003).

M. E. Stewart, C. R. Anderton, L. B. Thompson, J. M. Stephen, K. Gray, J.A. Rogers, and R. G. Nuzzo, Chem. Rev. 108(2), 494 (2008).

"Electrides: Ionic Salts with Electrons as the Anions," J. L. Dye, Science 247(4943), 663 (1990).

"Electrons as Anions," J. L. Dye, Science 301(5633), 607-608 (2003).

"High-Density Electron Anions in a Nanoporous Single Crystal: [Ca24Al28O64]4+(4e−)," S. Matsuishi, Y. Toda, M. Miyakawa, K. Hayashi, T. Kamiya, M. Hirano, I. Tanaka, and H. Hosono, Science 301(5633), 626-629 (2003).

K. L. Narrod, M. Leo, M. Sudnik, D. Rousell, and K. L. Rowlen, Appl. Spectrosc. 61(7), 994-1001 (1997).

S. W. Kim, S. Matsuishi, M. Miyakawa, K. Hayashi, M. Hirano, and H. Hosono, J. Mater, Sci.: Mater Electron, 18, 5-14 (2007).

"Surface-Enhanced Enfrared Spectroscopy," R. F. Aroca, D. J. Ross, and C. Domingo, Appl. Spectrosc, 58, 324-338 (2004).

"Surface Enhanced Raman Spectroscopy of Organic Molecules Deposited on Gold Sputtered Substrates," A. Merlen, V. Gadenne, J. Romann, V. Chevallier, L. Patrone, and J. C. Valmalette, Nanotechnology 20(21), 215705 (2009).

"The Effects of the Interaction between Resonances in the Electromagnetic Response of a Sphere-Plane Structure; Applications to Surface Enhanced Spectroscopy," P. K. Aravind and H. Metiu, Surf. Sci. 124(2-3), 506-528 (1983).

"Phonon-Enhanced Light-Matter Interation at the Nanometer Scale," R. Hillenbrand, T. Taubner, and F. Keilmann, Nature 418(6894), 159-162 (2002).

S. Matsuishi, S. W. Kim, T. Kamiya, M. Hirano, and H. Hosono, J. Phys. Chem. C 112(12), 4753-4760 (2008).

"Surface-Enhanced Raman Scattering: Physics and Applications," A. Otto and M. Futamata, Top. Appl. Phys. 103, 147-182 (2006).

"Surface Enhanced Infrared Absorption by Coupling Phonon and Plasmon Resonance," M. S. Anderson, Appl. Phys. Lett. 87(14), 144102 (2005).

"Plasphonics: Local Hybridization of Plasmons and Phonons," R. Marty, A. Miayah, A. Arbouet, C. Girard, and S. Tripathy, Opt. Express 21(4), 4551-4559 (2013).

* cited by examiner

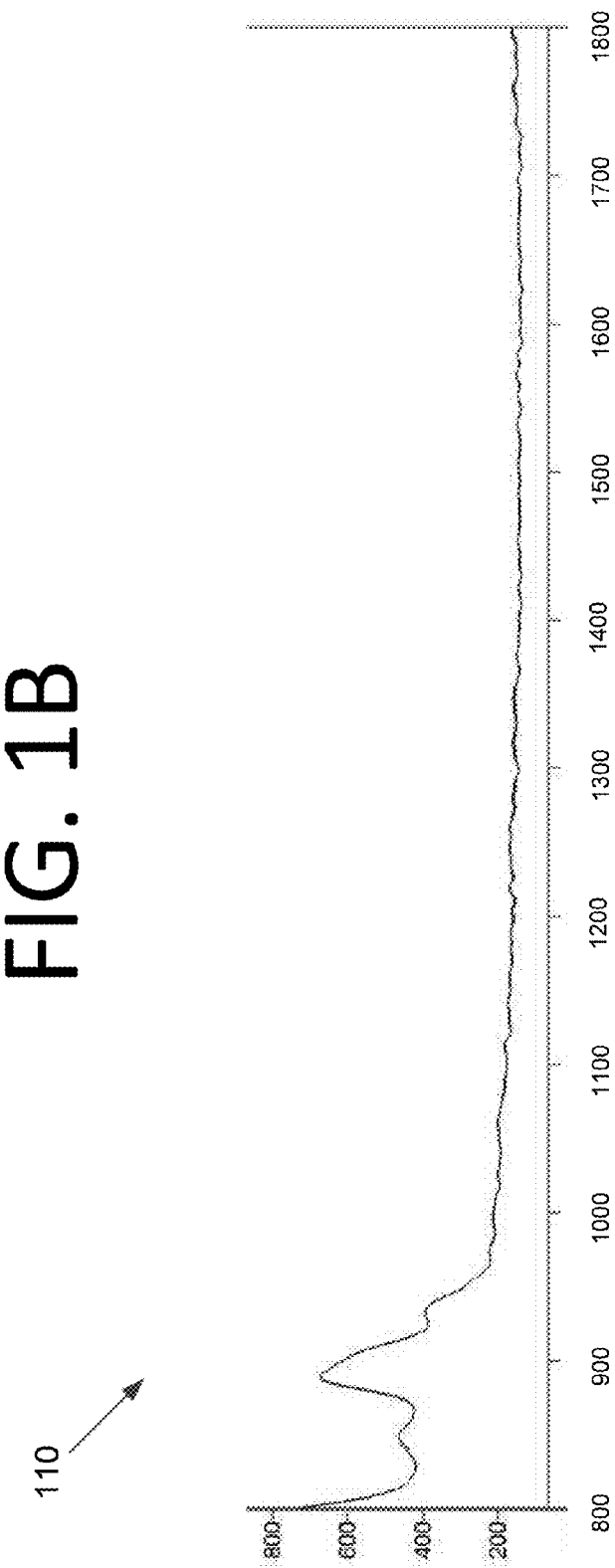

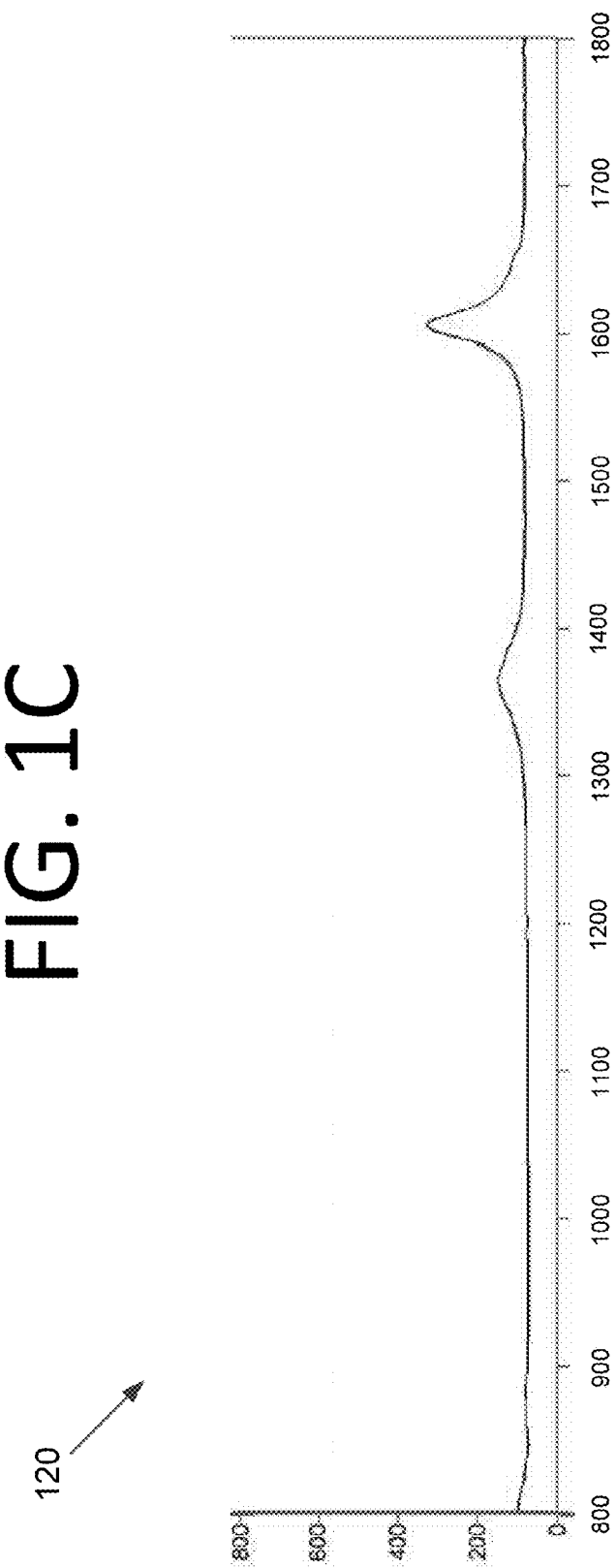

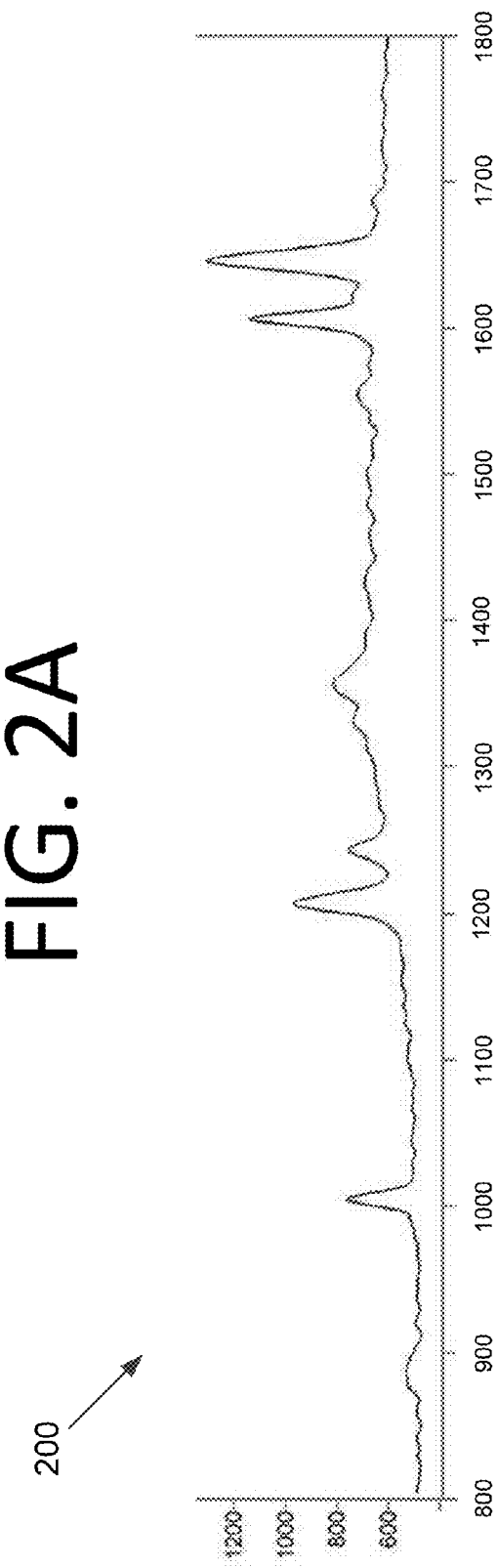

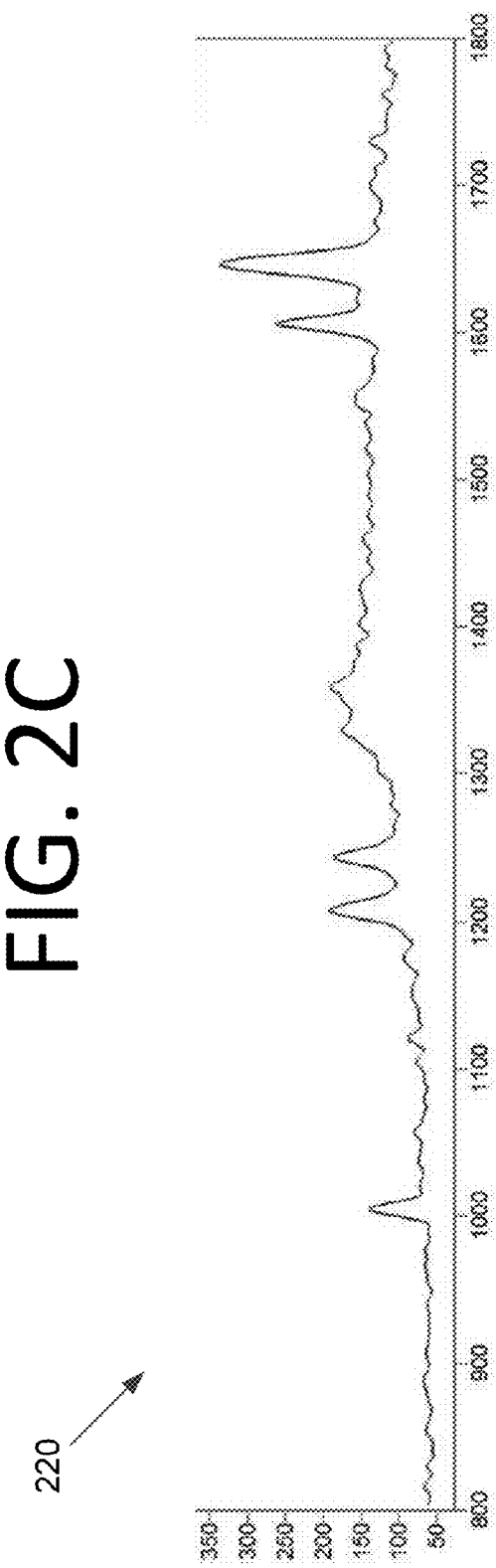

ELECTRIDE MEDIATED SURFACE ENHANCED RAMAN SCATTERING (SERS)

ORIGIN OF THE INVENTION

Embodiments of the present invention described herein were made in the performance of work under NASA contract NAS7-03001 and are subject to the provisions of Public Law #96-517 (35 U.S.C. §202) in which the Contractor has elected not to retain title.

FIELD

The present invention generally pertains to surface enhanced Raman scattering (SERS), and more specifically, to electride mediated SERS.

BACKGROUND

The enhanced optical fields near the surface of illuminated nanostructures form the basis of sensitive analytical methods that include SERS, tip-enhanced Raman spectroscopy (TERS), and surface enhanced infrared absorption. These methods exploit a surface plasmon resonance condition of special metallic nanostructures.

Early SERS efforts were based on rough silver electrodes. This was extended to gold and other metal nanostructures that were engineered to optimize the surface plasmonic interactions. In addition to surface plasmon resonance, there are other polariton resonance conditions that yield enhanced electric fields near the surface of illuminated nanostructures. Surface phonon resonance also provides enhanced optical fields near the surface of illuminated dielectric particles and is used for surface enhance infrared absorption spectroscopy. This is a part of a larger general effort to couple light into small device structures for photonic applications and for sensitive chemical analysis.

Conventional SERS applications use metal nanostructures. However, SERS applications that use electrides rather than metals may be beneficial.

SUMMARY

Certain embodiments of the present invention may be implemented and provide solutions to the problems and needs in the art that have not yet been fully solved by conventional SERS approaches. For instance, some embodiments texture the surface of an electride, such a ceramic electride or an organic electride, to facilitate enhanced SERS.

In one embodiment of the present invention, an apparatus includes an electride substrate comprising a textured surface. The apparatus also includes an analyte coated over at least part of the textured surface of the electride substrate.

In another embodiment of the present invention, an apparatus includes a ceramic electride substrate comprising $[CA24Al28O64]+4(4e-)$. The ceramic electride substrate has a roughened surface including cleaved beads. The apparatus also includes an analyte including trans-1,2-bis(4-pyridyl)ethylene (BPE). The analyte is coated over at least part of the roughened surface of the ceramic electride substrate.

In yet another embodiment of the present invention, a method includes cleaving beads of an electride substrate to produce textured areas. The method also includes coating the rough areas of the electride substrate with an analyte.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 1B is a graph illustrating counts versus Raman shift $(cm^{-1})$ for a smooth area of the BPE film of FIG. 1A with no SERS activity, according to an embodiment of the present invention.

FIG. 1C is a graph illustrating counts versus Raman shift $(cm^{-1})$ for rough mayenite of the BPE film of FIG. 1A, according to an embodiment of the present invention.

FIG. 2A is a graph illustrating counts versus Raman shift $(cm^{-1})$ for a top spectrum of SERS of a thin (1 nm) BPE film on an electride powder, according to an embodiment of the present invention.

FIG. 2C is a graph illustrating counts versus Raman shift $(cm^{-1})$ for a thick (10 μm) BPE reference film with no SERS, according to an embodiment of the present invention.

DETAILED DESCRIPTION OF THE EMBODIMENTS

Figure 5:
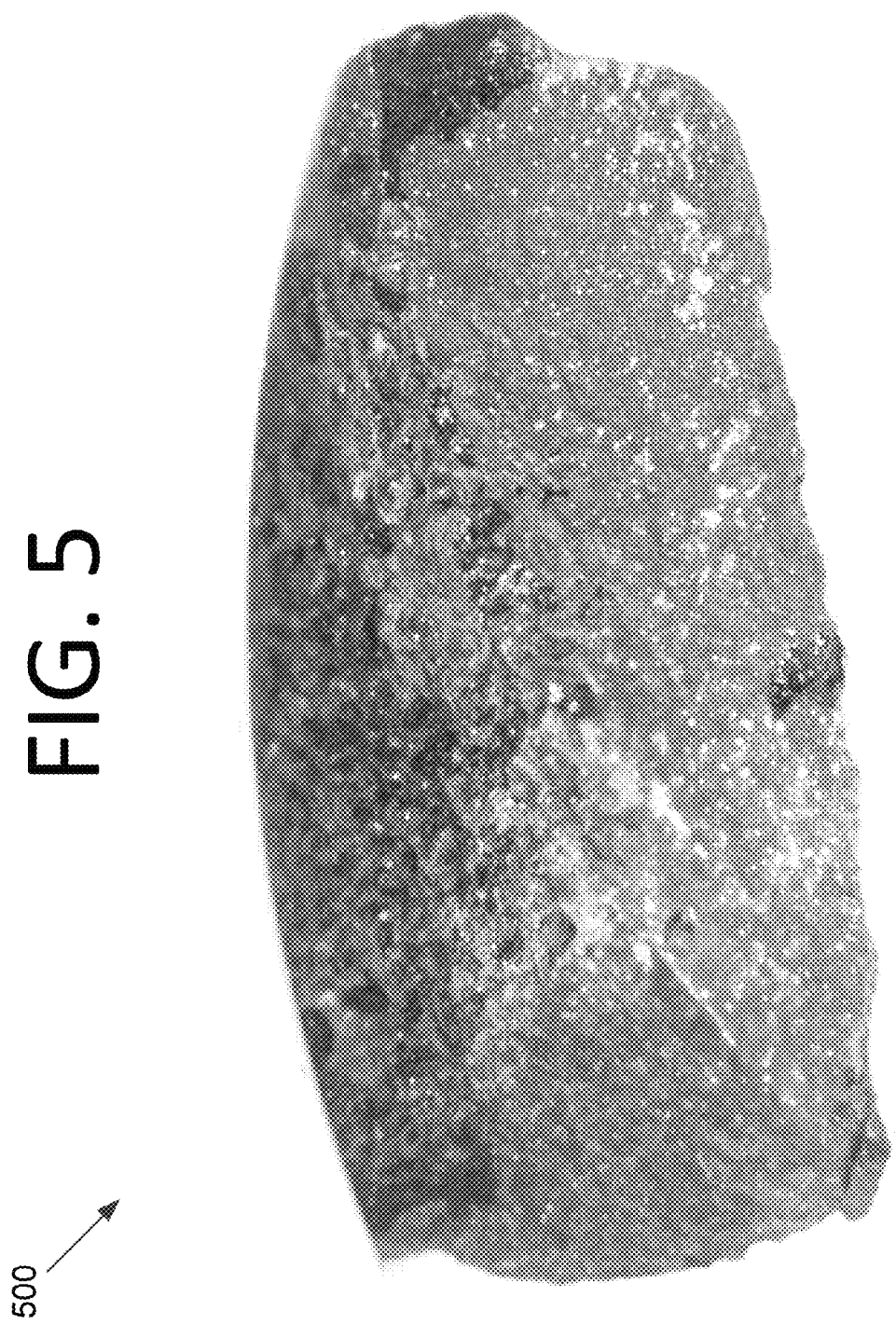
FIG. 5 is an image of an electride surface, according to an embodiment of the present invention.

Some embodiments use a ceramic or organic electride to facilitate enhanced SERS. For instance, certain embodiments texture the surface of the electride, such as a mayenite-derived ceramic electride, to produce a rough electride surface and facilitate enhanced SERS. After the electride is synthesized, "beads" are produced. These beads are then cleaved. See image 500 of FIG. 5. When coated with a Raman active analyte, the rough areas of the electride have greatly enhanced Raman scattering. The rough areas act like nano-antennas and create an enhanced electric field. Such embodiments may provide a sensitive method for monitoring the chemistry and electronic environment at the electride surface.

Electrides are a class of ionic compounds where electrons are not localized on specific atoms or molecules, but occupy sites typically populated by anions. In electrides, the electrons are not completely delocalized as in metals and may be regarded as a crystalline form of solvated electrons. Electrons occupying the anionic sites have unusual properties as a result of their small mass compared to typical anions. A surface "electride-plasmon" resonance forms the basis of electride-mediated SERS in some embodiments. This is distinct from the surface plasmon-polariton resonance mediating conventional SERS.

The electride substrate used in some embodiments may be a mayenite derived ceramic compound, $[CA24Al28O64]^{+4}$ (4e−), that is thermally stable and relatively unreactive. The analyte may be trans-1,2-bis(4-pyridyl)ethylene (BPE) cast as a thin film on a roughened electride surface or on the powdered electride. However, other suitable electrides and analytes may be used, as would be understood by one of ordinary skill in the art. BPE has been previously used to quantitatively compare SERS substrates and lacks resonant enhancement in the visible region. BPE was tested for SERS using 532 nm and 785 nm laser excitation frequencies. The surface enhanced Raman spectra of thin BPE films on the electride was compared to an unenhanced spectrum of a thick BPE film and the conventional SERS spectrum of BPE on a sputtered gold substrate.

The synthesis of the ceramic electride $[CA24Al28O64]^{+}4(4e-)$ in some embodiments uses a high temperature processing of the mayenite precursor $(CaO)_{12}(Al_2O_3)_7$ by sintering stoichiometric proportions of calcium carbonate and aluminum oxide at 1300° C.-1400° C. in oxygen. The mayenite precursor may then be chemically reduced to form the electride by heat cycling past its melting point (~1415° C.) to 1600° C. in a sealed, carbon containing vessel. The synthesized electride may be in the form of ~5 mm sized beads that may then be cleaved in half using a clean razor blade and tapping with a small mallet under nitrogen. See image 500 of FIG. 5, which shows an electride surface. This fracturing method produced areas that greatly vary in surface roughness. Smooth glassy areas are often adjacent to rough areas (within 10-20 µm). When coated simultaneously with a test compound (e.g., trans-1,2-bis(4-pyridyl)ethylene (BPE) or generic analytes that are SERS active), these smooth and rough areas can be directly compared for SERS activity. The electride may be stored under dry nitrogen and the top surface may be cleaved away immediately before testing.

Raman spectroscopy may be performed with any suitable system, such as a Bruker Senterra (Bruker Optics, Billerica, Mass.) system equipped with 532 nm and 785 nm lasers. The samples may be interrogated using the 20× objective and the spectra may be acquired using 5 second integrating times and 10 co-additions at a resolution of 4 wavenumbers. The 532 nm laser may be set at a 2 mW power level and the 785 nm laser may be set at a 10 mW power level. The spot size may be approximately 2 µm. To test for SERS activity, a thin (~1 nm) film of BPE (e.g., Aldrich 99.9%) may be deposited on the SERS substrate using the "drop-drying method" from a dilute isopropanol (Aldrich) solution using a micro-syringe. For comparison, conventional SERS substrates may be prepared by sputtering gold onto aluminum oxide supported on aluminum using a sputtering procedure.

The visible spectra may be acquired using a Cary 5E spectrometer (Agilent, Santa Clara, Calif.), or any other suitable spectrometer. A white spectrally flat polytetrafluoroethylene (PTFE) coated integrating sphere and a spectralon PTFE reference (Labsphere, North Sutton, N.H.) may be used. The sample particles may be dispersed on a PTFE substrate and the total hemispherical reflectance may be measured from 400 nm and 800 nm. The samples may be in the form of finely ground powders on a spectrally neutral, PTFE substrate to better reveal the surface modes. This dilution may be necessary to prevent optical saturation of the strongly absorbing, pure sample.

Figure 1A:
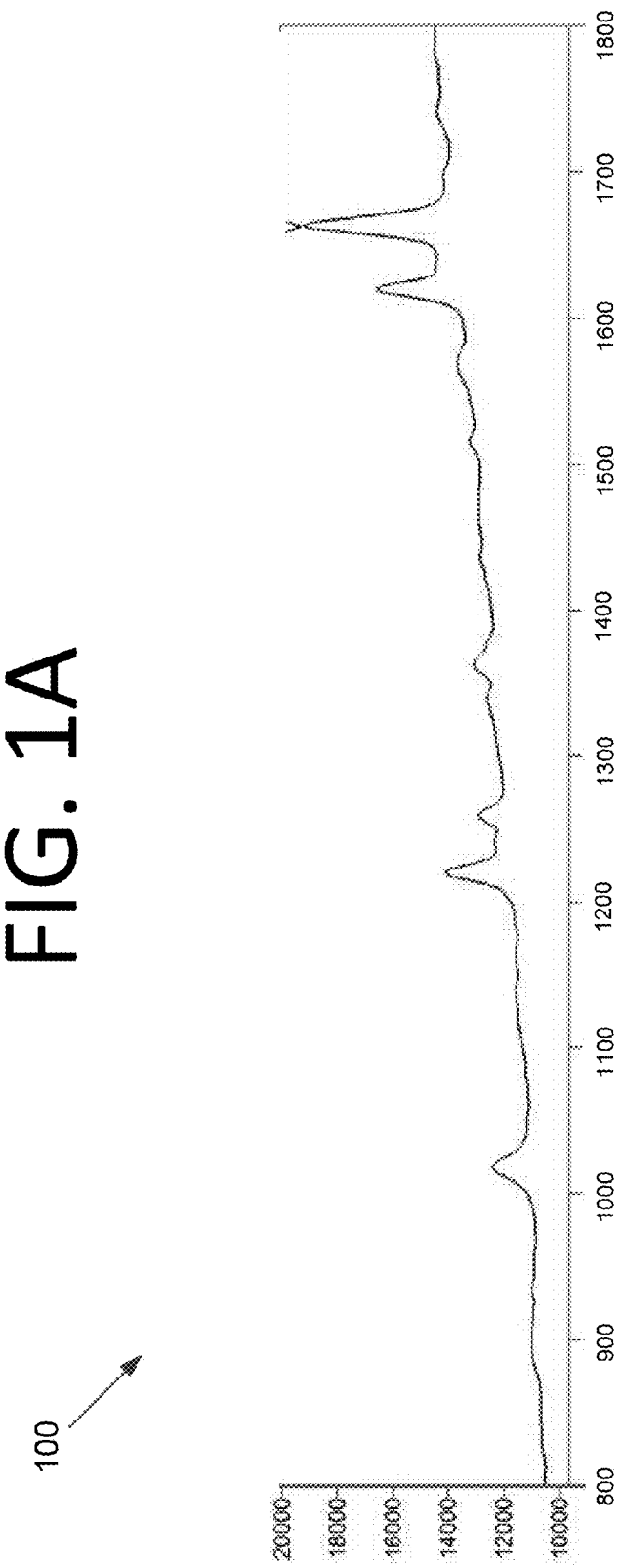
FIG. 1A is a graph illustrating counts versus Raman shift $(cm^{-1})$ for a ~1 nm BPE film on rough, textured regions of a fractured electride surface, according to an embodiment of the present invention.
Figure 1D:
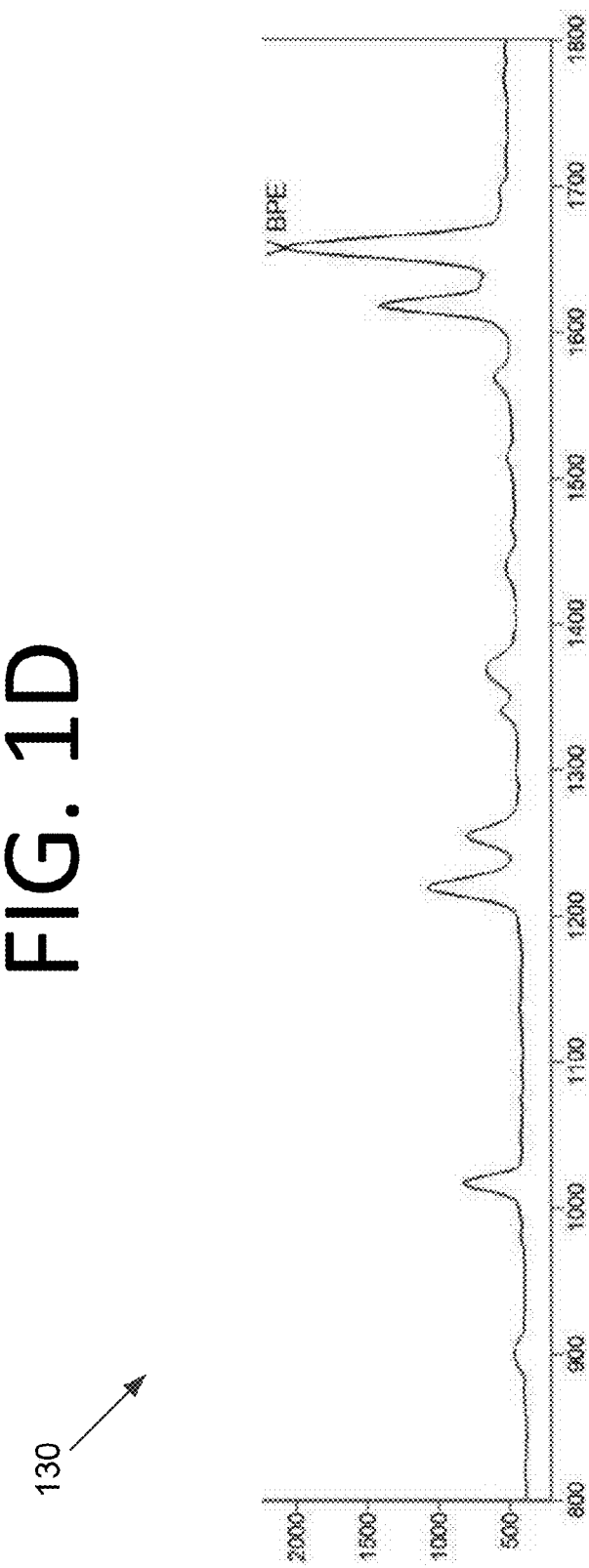
FIG. 1D is a graph illustrating counts versus Raman shift $(cm^{-1})$ for a thick (10 μm) BPE reference film with no SERS, according to an embodiment of the present invention.

In graphs 100-130 of FIGS. 1A-D, BPE was used with 532 nm excitation. The SERS spectrum of a ~1 nm BPE film maybe readily obtained on the rough, textured regions of the fractured electride surface as shown in graph 100 of FIG. 1A. Smooth, evenly cleaved areas did not produce SERS activity. See graph 110 of FIG. 1B. In order to show that the enhanced signal is not due to the rough surface, the BPE analyte may be similarly deposited on a rough, partially reduced mayenite (see graph 120 of FIG. 1C). As shown in FIG. 1C, this did not produce a detectable Raman signal of BPE and the enhancement due to surface roughness alone can be ruled out. Using a thick (~10 µm), unenhanced BPE film on a mirror as a reference (see graph 130 of FIG. 1D), SERS enhancement can be bounded to be greater than $10^4$ for the 532 nm excitation. The SERS enhancement, based on theoretical and experimental work, occurs less than 25 nm from the substrate surface.

Figure 2B:
FIG. 2B is a graph illustrating counts versus Raman shift $(cm^{-1})$ for SERS of BPE on plasma sputtered gold, according to an embodiment of the present invention.

The electride mediated SERS at 785 nm excitation is given in graphs 200-220 of FIGS. 2A-C. The electride's SERS enhancement factor at 785 nm excitation is bounded to be greater than $10^3$. This is similar to the conventional SERS BPE spectrum from sputtered gold. As expected for SERS, both the electride mediated SERS and sputtered gold mediated SERS spectra have somewhat different peak ratios from the unenhanced reference BPE.

Figure 3:
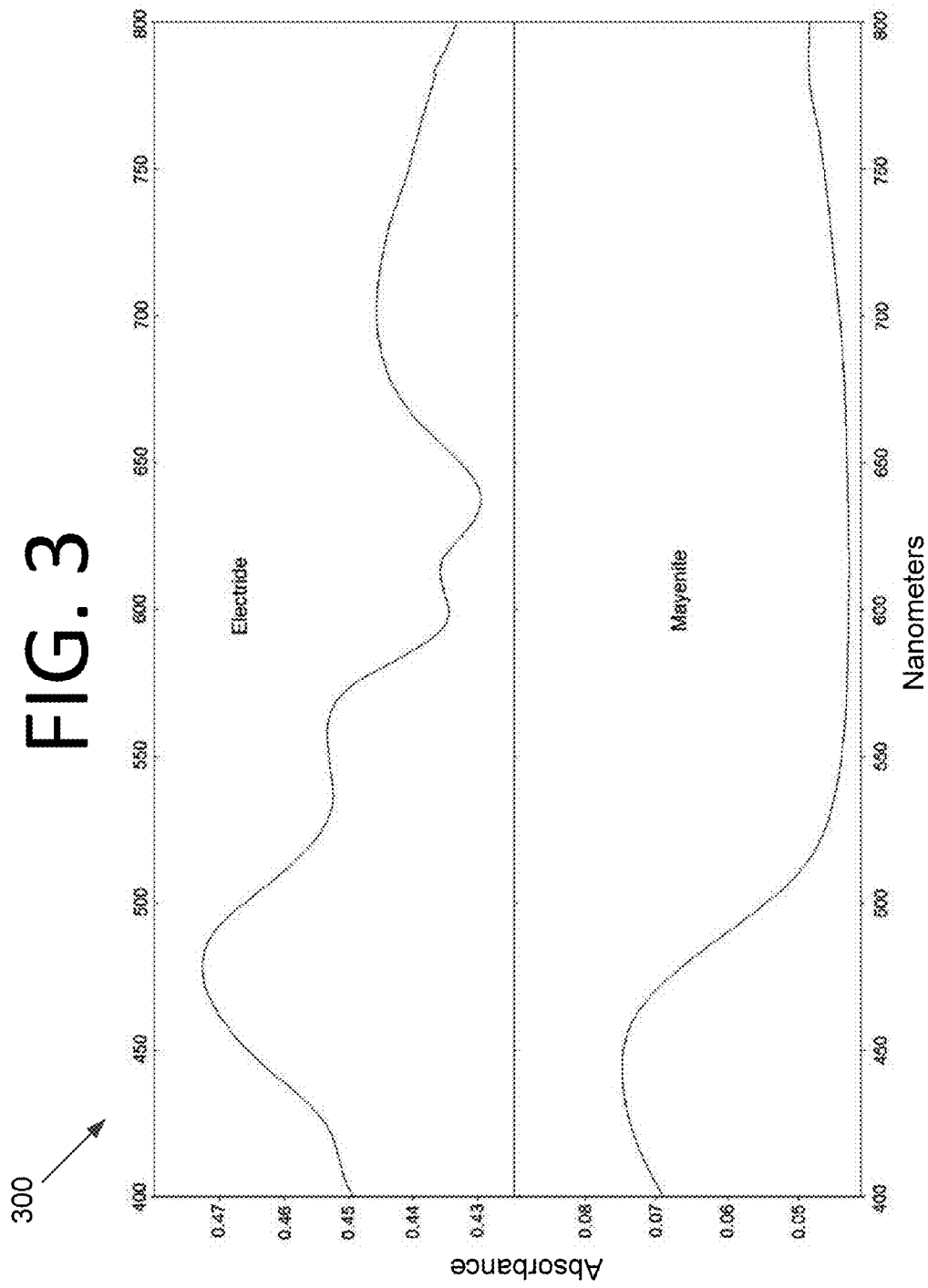
FIG. 3 is a graph illustrating visible reflectance spectra for an electride powder (top) and a partially reduced mayenite precursor (bottom), according to an embodiment of the present invention.

In addition to SERS demonstrated in FIGS. 1A-D and 2A-C, the electride was examined by the visible reflectance to reveal surface plasmon resonances. This approach is also used for characterization of metallic SERS substrates. The spectra of partially reduced mayenite and the reduced electride are compared in the 400 nm to 800 nm wavelength range (see graph 300 of FIG. 3). The visible reflectance spectra are shown for the electride powder (top) and the partially reduced mayenite precursor (bottom). The electride has additional peaks at 479 nm, 561 nm, 614 nm, and 702 nm. The surface modes of the fully reduced electride are revealed in the visible wavelength range. The frequencies of these surface modes may be shifted somewhat depending on the size, shape, and aggregation of the particles.

The SERS activity of the electride measured at 532 nm and 785 nm excitation frequencies corresponds with the broad overlapping peaks seen in reflectance spectrum of the powder at 560 nm and 702 nm, respectively. Taken together, this provides evidence of a surface plasmon resonance at visible frequencies. The surface plasmon resonances should be shifted from the bulk plasma resonance depending on the size, shape, and aggregation of the surface features. The difference between the surface plasmon resonance of conventional SERS using metals and electride mediated SERS depends on the differences in the electronic structure of conductive electrides and metals. The electronic states in the mayenite-based electride were previously analyzed by optical reflectance spectra using the Drude-Lorentz model.

In summary, for electride precursors that are not fully reduced, the electrons are localized in the cages of F+ centers in CaO (F+ states). The electrons move by hopping as polarons, with conductive activation energy of 0.1 eV. The more fully reduced, higher conductivity electride has a higher density of F+ states forming more delocalized bands that overlap the cage conduction band with both localized and delocalized electrons. The electride has metallic conduction and a more Drude-type response that dominates with the electrons delocalized over the ceramic cage. The mayenite electride has weak localization behavior and a small temperature dependence of electrical conductivity near room temperature. This fully reduced form would be expected to be the most SERS active material.

Put in a more general context, surface plasmon-polaritons in certain metals mediate the electromagnetic contribution of conventional SERS. Polaritons are formed by the strong coupling of electromagnetic waves with an electric or magnetic dipole-carrying excitation and are considered a form of quasi-particle. SERS in some embodiments has been demonstrated using an electrode. The distinction between this surface electride-polariton and a surface plasmon-polariton lies in the differences in the nature of the anionic electrons in an electride and electrons in a metallic conductor.

In addition to the electromagnetic resonance enhancement underlying SERS, there is a chemical enhancement component that is attributed to a charge transfer from the analyte to the substrate. The chemical enhancement contribution to SERS depends on the nature of the absorbed analyte and the substrate. Electrides have a low work function compared to the metals used in conventional SERS. Therefore, electrides would have a different charge transfer potential than metal substrates that mediated conventional SERS.

SERS activity may also serve as a probe of the electride surface and not just for detection of absorbed analytes. The synthesis of a fully reduced electride with the highest conductivity at the surface is a goal in electride development. Samples that are not fully reduced, or have reacted with the environment, will have regions that are less conductive and will not support SERS.

As a result of their low work function, electrides may be used as chemical reducing agents. Electride mediated SERS may serve to monitor chemical reduction at the electride surface.

As demonstrated herein, micron-sized regions may be interrogated with the Raman microprobe. It should be noted that Tip Enhanced Raman Spectroscopy (TERS) method, which exploit SERS at the nanometer scale, could provide an even finer probe of the electride surface. TERS is SERS accomplished with a probe microscope tip. Thus, an electride tip is conceivable to achieve TERS/SERS. TERS is going down a path of applying a SERS active electride tip for probe microscopes. Electrides serving as probe microscope tips is a particular application of electride-mediated SERS.

The rough electride surfaces interrogated in some embodiments, as with early SERS efforts using roughened silver, may not be optimized for maximum enhancement. Larger enhancements are expected if the electride surface morphology or electride particle sizes are properly tuned to the particular Raman excitation laser used in a given application. Further work is planned to examine the surface enhanced infrared properties of the electride at wavelengths where the electride-polariton and the electride-phonon resonances overlap. These various surface polariton resonances of plasmons, phonons, excitons, and electride-polaritons, may be coupled together in hybrid structures.

Figure 4:
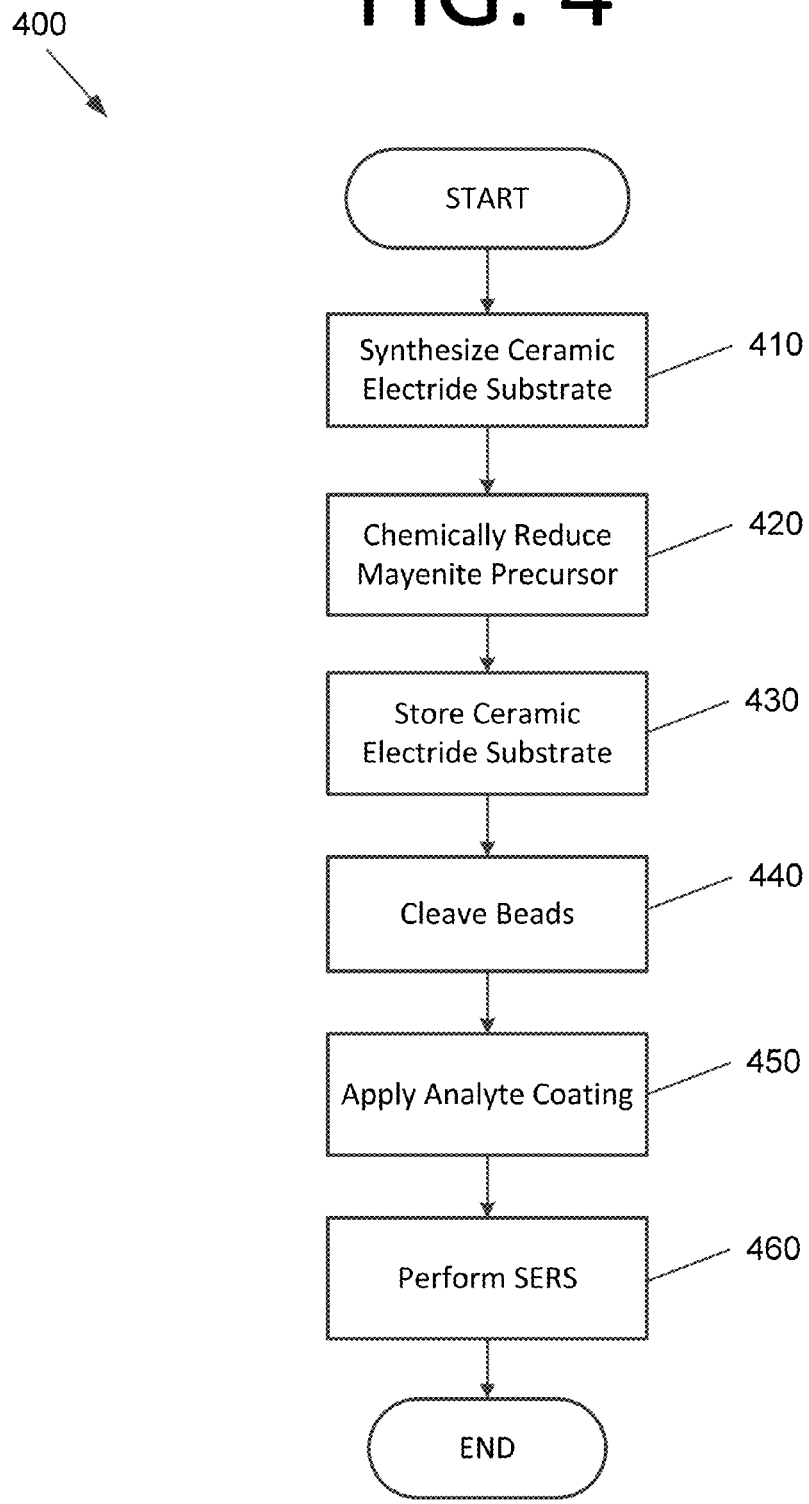
FIG. 4 is a flowchart illustrating a method for producing a textured ceramic electride, according to an embodiment of the present invention.

FIG. 4 is a flowchart 400 illustrating a method for producing a textured ceramic electride, according to an embodiment of the present invention. However, in other embodiments, other ceramic electrides or organic electrides may be used. The method begins with synthesizing a ceramic electride substrate at 410 via high temperature processing of mayenite precursor $(CaO)12(Al2O3)7$ by sintering stoichiometric proportions of calcium carbonate and aluminum oxide at 1300° C.-1400° C. in oxygen. Next, the mayenite precursor is chemically reduced at 420 to form the ceramic electride substrate by heat cycling past its melting point to 1600° C. in a sealed, carbon containing vessel. The ceramic electride substrate is then stored under dry nitrogen at 430.

Beads of the ceramic electride substrate are cleaved at 440 to produce textured areas. The rough areas of the ceramic electride substrate are coated with an analyte at 450. SERS is then performed on the coated ceramic electride substrate at 460. In some embodiments, the SERS may be performed using 532 nm and 785 nm excitation frequencies.

It will be readily understood that the components of various embodiments of the present invention, as generally described and illustrated in the figures herein, may be arranged and designed in a wide variety of different configurations. Thus, the detailed description of the embodiments of the systems, apparatuses, methods, and computer programs of the present invention, as respresented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus to enhance a target analyte for detection via Raman scattering, comprising:
   a Raman spectroscopy system;
   a substrate comprising an electrode material having a textured surface, the substrate positioned to be interrogated by the Raman spectroscopy system; and
   the target analyte coated over at least part of the textured surface of the electrode substrate to enhance detection of the target analyte for Raman scattering.

2. The apparatus of claim 1, wherein the textured surface is formed from cleaving beads off the substrate.

3. The apparatus of claim 2, wherein the beads are cleaved using a clean razor blade and tapping with a small mallet under nitrogen.

4. The apparatus of claim 1, wherein the substrate comprises an organic electrode or a ceramic electrode.

5. The apparatus of claim 1, wherein the electrode comprises mayenite derived ceramic compound [Ca24Al28O64]+4(4e−).

6. The apparatus of claim 1, wherein the analyte comprises trans-1,2-bis(4-pyridyl)ethylene (BPE).

7. The apparatus of claim 1, wherein the analyte is cast as a thin film on the textured surface or on a powdered electrode.

8. The apparatus of claim 1, wherein the substrate is synthesized via high temperature processing of mayenite precursor $(CaO)_{12}(Al_2O_3)_7$ by sintering stoichiometric proportions of calcium carbonate and aluminum oxide at 1300° C. to 1400° C. in oxygen.

9. The apparatus of claim 8, wherein the mayenite precursor is chemically reduced to form the electrode substrate by heat cycling past its melting point to 1600° C. in a sealed, carbon containing vessel.

10. The apparatus of claim 1, wherein the ceramic electride substrate is synthesized via high temperature processing of mayenite precursor $(CaO)_{12}(Al_2O_3)_7$ by sintering stoichiometric proportions of calcium carbonate and aluminum oxide at 1300° C. to 1400° C. in oxygen.

11. The apparatus of claim 10, wherein the mayenite precursor is chemically reduced to form the ceramic electride substrate by heat cycling past its melting point to 1600° C. in a sealed, carbon containing vessel.

12. An apparatus, comprising:
   a ceramic electrode substrate comprising [Ca24Al28O64]+4(4e−), the ceramic electrode substrate having a roughened surface comprising cleaved beads; and
   an analyte comprising trans-1,2-bis(4-pyridyl)ethylene (BPE), the analyte coated over at least part of the roughened surface of the ceramic electride substrate.

13. The apparatus of claim 12, wherein the beads are cleaved using a clean razor blade and tapping with a small mallet under nitrogen.

14. The apparatus of claim 12, wherein the analyte is cast as a thin film on the roughened surface or on a powdered electrode.

15. A method to enhance Raman scattering in a Raman spectroscopy system, comprising:
   cleaving beads off a substrate comprising an electrode material to produce textured areas; and
   coating the textured areas of the substrate with an analyte; and,
   performing surface enhanced Raman spectroscopy (SERS) on the coated substrate.

16. The method of claim 15, wherein the SERS is performed using 532 nm and 785 nm excitation frequencies.

17. The method of claim 15, further comprising:
   synthesizing the substrate via high temperature processing of mayenite precursor $(CaO)_{12}(Al_2O_3)_7$ by sintering stoichiometric proportions of calcium carbonate and aluminum oxide at 1300° C. to 1400° C. in oxygen.

18. The method of claim 17, further comprising:
   chemically reducing the mayenite precursor to form the substrate by heat cycling past its melting point to 1600° C. in a sealed, carbon containing vessel.

19. The method of claim 15, further comprising:
   storing the substrate under dry nitrogen.

* * * * *